(12) United States Patent
Mitsunaka et al.

(10) Patent No.: US 10,816,536 B2
(45) Date of Patent: Oct. 27, 2020

(54) BIOPARTICLE OBSERVATION APPARATUS AND BIOPARTICLE OBSERVATION METHOD

(71) Applicants: SHARP KABUSHIKI KAISHA, Sakai, Osaka (JP); KYOTO UNIVERSITY, Kyoto-shi, Kyoto (JP)

(72) Inventors: Takeshi Mitsunaka, Sakai (JP); Yuichi Ogawa, Kyoto (JP)

(73) Assignees: SHARP KABUSHIKI KAISHA, Sakai, Osaka (JP); KYOTO UNIVERSITY, Kyoto-shi, Kyoto (JP)

( * ) Notice: Subject to any disclaimer, the term of this patent is extended or adjusted under 35 U.S.C. 154(b) by 0 days.

(21) Appl. No.: 16/436,338

(22) Filed: Jun. 10, 2019

(65) Prior Publication Data

US 2019/0376947 A1 Dec. 12, 2019

(30) Foreign Application Priority Data

Jun. 11, 2018 (JP) .................................. 2018-111342

(51) Int. Cl.
*G01N 33/00* (2006.01)
*G01N 33/483* (2006.01)
*G01N 21/01* (2006.01)

(52) U.S. Cl.
CPC ......... *G01N 33/4833* (2013.01); *G01N 21/01* (2013.01)

(58) Field of Classification Search
CPC ............... G01N 33/4833; G01N 21/01; G01N 15/1484; G01N 15/1031; G01N 2015/1006; B03C 5/026; B03C 5/005; B03C 2201/26; G01B 7/14
USPC ...... 250/492.1, 251, 281, 282; 204/450, 452
See application file for complete search history.

(56) References Cited

U.S. PATENT DOCUMENTS

| | | | |
|---|---|---|---|
| 2007/0221501 A1* | 9/2007 | Schnelle | B03C 5/026 204/547 |
| 2009/0092989 A1* | 4/2009 | Chang | B03C 5/005 435/6.14 |
| 2015/0224496 A1* | 8/2015 | Guerrieri | B01L 3/50273 204/452 |
| 2019/0242845 A1* | 8/2019 | Saito | G01N 15/0656 |

FOREIGN PATENT DOCUMENTS

JP 2005-080579 A 3/2005

\* cited by examiner

*Primary Examiner* — Michael Maskell
(74) *Attorney, Agent, or Firm* — ScienBiziP, P.C.

(57) ABSTRACT

A bioparticle observation apparatus includes a dielectrophoresis electrode that outputs a first signal causing a dielectrophoresis force to act on a bioparticle, a sensor electrode that detects an impedance difference between the bioparticle and the liquid, and a control circuit that controls the first signal so that the detected impedance difference is fixed.

16 Claims, 4 Drawing Sheets

BIOPARTICLE OBSERVATION APPARATUS AND BIOPARTICLE OBSERVATION METHOD

BACKGROUND

1. Field

The present disclosure relates to a bioparticle observation apparatus and a bioparticle observation method that are used to observe fine bioparticles in liquid.

2. Description of the Related Art

In accordance with an existence form in cell culture, cells, which are one kind of bioparticle, are roughly classified into one kind called adherent cells, which adhere to a culture container and grow, and another kind called suspended cells, which grow in a state of being suspended in a medium.

When observing a suspended cell such as a hematopoietic cell by using a microscope to trace a growth pattern, an observation target is to be fixed at a predetermined position. For observing the suspended cell under the microscope, a method of setting aside the suspended cell, which is in a medium, in a dish or the like for observation is considered, but when culture and observation using the microscope are performed for a long time, a suspended state is not maintained and the cells are thus greatly damaged.

On the other hand, as a proposal for fixing the suspended cells, as illustrated in FIG. 7, a method of forming a fixing agent 201, such as a protein or a polymer, that has excellent compatibility with a surface of a cell 200 in solution 203 and thereby fixing the cell surface to a dish 202 or the like is known. Since a cell wall of the cell 200 is not directly bonded to a bottom surface of the dish 202 or the like, a suspended state is maintained, even after culture and observation are performed for a long time. The observation is performed through a lid 204 such as a cover glass. According to the aforementioned configuration, less damage to the cell is expected. For example, Japanese Unexamined Patent Application Publication No. 2005-80579 (published on Mar. 31, 2005) proposes a method in which the fixing agent 201 has a phosphorylcholine-like group and a hydrazide group. With the method, a protein that fixes the suspended cell to the dish or the like is modified in advance and is bonded and mixed with the surface of the suspended cell for fixation. This makes it possible to fix the surface of the cell 200 to the dish 202 or the like.

However, with the method of fixing the suspended cell according to the related art disclosed in Japanese Unexamined Patent Application Publication No. 2005-80579 described above, it is difficult to selectively fix a type of cell among a plurality of types of cell by using protein to be modified or to fix only a single cell, which poses a problem of fixing a plurality of cells at the same time in many cases. The method of fixing the suspended cell according to the related art also has problems in which it is difficult to observe behavior of a single cell under the microscope and in which there is a concern about damage to the cells because a plurality of cells are intensively fixed.

An aspect of the disclosure is made in view of the problems of the related art described above and provides a bioparticle observation apparatus and the like that are able to reduce damage to bioparticles and facilitate observation of a single bioparticle.

SUMMARY

A bioparticle observation apparatus according to an aspect of the disclosure is a bioparticle observation apparatus usable for observing a bioparticle in liquid, and includes: a dielectrophoresis electrode that outputs a first signal causing a dielectrophoresis force to act on the bioparticle; a sensor electrode that detects an impedance difference between the bioparticle and the liquid; and a control circuit that controls the first signal so that the detected impedance difference is fixed.

DESCRIPTION OF THE EMBODIMENTS

Embodiment 1

Figure 1:
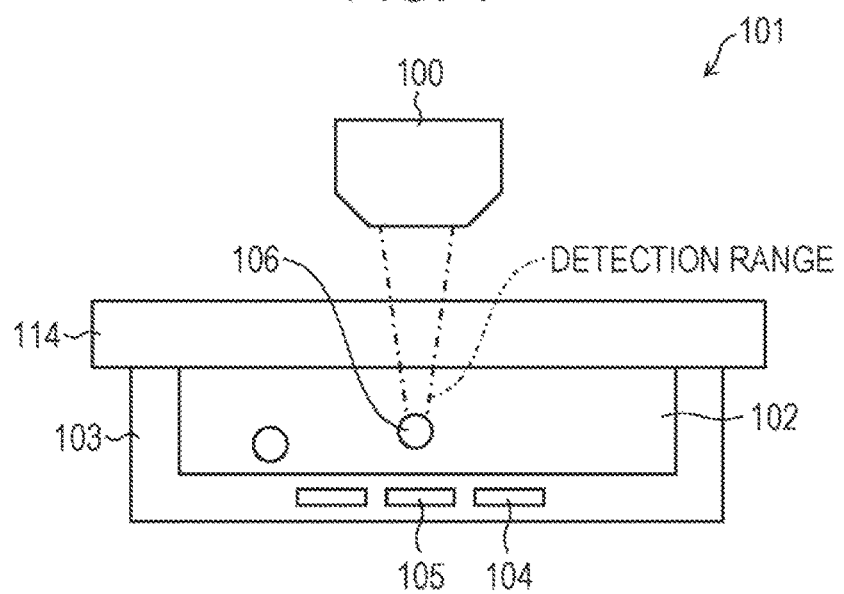
FIG. 1 is a schematic view illustrating an outline configuration of a bioparticle observation apparatus according to Embodiment 1 of the disclosure.

A bioparticle observation apparatus 101 according to Embodiment 1 of the disclosure will be described below with reference to FIG. 1. The bioparticle observation apparatus 101 of the present embodiment relates to an apparatus that observes, by using a microscope 100 or the like, a bioparticle 106, such as a cell or a bacterium, which is suspended in a solution such as a medium. The bioparticle observation apparatus 101 is used mainly for research, clinical testing, and the like in biology and medicine.

More specifically, the bioparticle observation apparatus 101 observes, by using the microscope 100, the bioparticle 106 suspended in a solution (liquid) 102 in a container 103. A lid 114 such as a cover glass may be provided on the top of the container 103.

Moreover, the bioparticle observation apparatus 101 of the present embodiment includes at least a dielectrophoresis electrode 104 and a sensor electrode 105 in a bottom surface of the container 103 in which the solution 102 such as the medium is storing. The dielectrophoresis electrode 104 is an electrode that outputs a signal (first signal) $V_{DEP1}$ which causes a dielectrophoresis force to act on the bioparticle 106. The sensor electrode 105 is an electrode for detecting an impedance difference between the bioparticle 106 and the solution 102. Note that, the sensor electrode 105 may be a single electrode as illustrated in FIGS. 2A to 2C or may be a differential electrode (not illustrated).

Figure 2A:
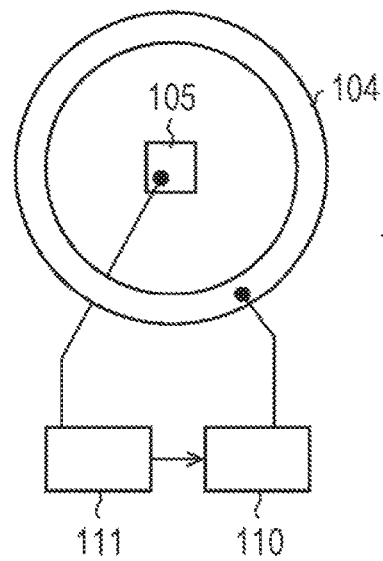
FIGS. 2A to 2C are schematic views illustrating variations in arrangement of a dielectrophoresis electrode in the bioparticle observation apparatus.
Figure 2B:
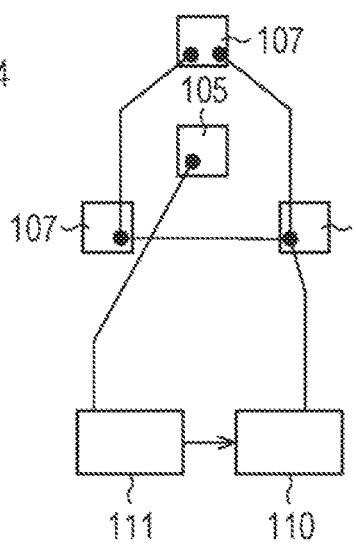
Figure 2C:
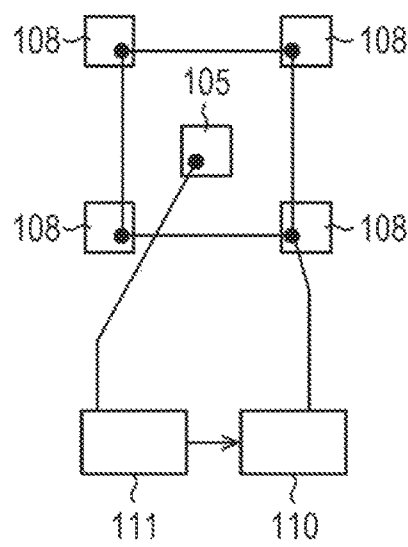

Next, FIG. 2A illustrates a vicinity of a region where the dielectrophoresis electrode 104 and the sensor electrode 105 are arranged when the bottom surface of the container 103 is seen from above.

In the bioparticle observation apparatus 101, the dielectrophoresis electrode 104 surrounds the sensor electrode 105. FIG. 2A illustrates the dielectrophoresis electrode 104 formed to surround, in a circular shape, a periphery of the sensor electrode 105 with the sensor electrode 105 located at a center, but the dielectrophoresis electrode 104 may be formed to surround, in a polygonal shape, the periphery of the sensor electrode 105 with the sensor electrode 105 located at the center.

Though the container 103 is filled with the solution 102 such as the medium, the bioparticle 106 such as a cell or a bacterium that is suspended is a suspended cell.

A dielectrophoresis force $F_{DEP}$ that the dielectrophoresis electrode 104 applies to the bioparticle 106 is represented by, in general, the following formula (1).

$$F_{DEP} = 2\pi \left(\frac{d}{2}\right)^3 \varepsilon_m \text{Re}\left[\frac{\varepsilon_p^* - \varepsilon_m^*}{\varepsilon_p^* - 2\varepsilon_m^*}\right] FE^2 \quad (1)$$

where d is a diameter of a single bioparticle 106, $\varepsilon_p^*$ and $\varepsilon_m^*$ are complex dielectric constants of the bioparticle 106 and the solution 102, respectively and E is an electric field applied by the dielectrophoresis electrode 104.

In accordance with a positive or negative sign of a real number component of $$\frac{\varepsilon_p^* - \varepsilon_m^*}{\varepsilon_p^* - 2\varepsilon_m^*},$$

which is a CM factor, it is possible to calculate whether the dielectrophoresis force of the dielectrophoresis electrode 104 attracts or repels the bioparticle 106.

In the present embodiment, a force (a negative dielectrophoresis force) repelling the bioparticle 106 from the dielectrophoresis electrode 104 is used. Since the bioparticle 106 represented by a cell generally has a higher density than the solution 102 such as the medium, the bioparticle 106 sinks in the liquid due to gravity. Here, when the signal (first signal) $V_{DEP1}$ that provides the negative dielectrophoresis force is applied to the dielectrophoresis electrode 104, the bioparticle 106 does not sink but remains suspended in the liquid.

The dielectrophoresis electrode 104 is configured to surround the sensor electrode 105 concentrically. The electric field generated by the dielectrophoresis electrode 104 is strongest at the dielectrophoresis electrode 104 and weakens in line with distance from the dielectrophoresis electrode 104. In a vicinity of the sensor electrode 105 surrounded by the dielectrophoresis electrode 104, the dielectrophoresis force acts in a direction to enable attraction to the sensor electrode 105 or in a direction to enable repulsion from the sensor electrode 105 in accordance with a size or a frequency of the electric field provided by the dielectrophoresis electrode 104, and thus the bioparticle 106 is retained in a part surrounded by the dielectrophoresis electrode 104 as viewed with the microscope 100 (i.e., from above the container 103).

A detection circuit 111 determines a distance between the sensor electrode 105 and the bioparticle 106 and causes a control circuit 110 to adjust a signal amplitude or a signal frequency of the signal $V_{DEP1}$. Note that, the direction of the dielectrophoresis force changes depending on the signal frequency. This is able to be determined in accordance with a positive or negative sign of a real part of the CM factor (mathematical formula 2). Moreover, when the signal amplitude varies, a repulsion force or an attraction force increases or decreases (refer to $\nabla E^2$ of mathematical formula 1). Since the direction and size of the repulsion force or attraction force vary depending on the dielectric constants ($\varepsilon_p^*$, $\varepsilon_m^*$) of a target cell and the suspending solution 102, the dielectrophoresis force depends on the environment.

Figure 4:
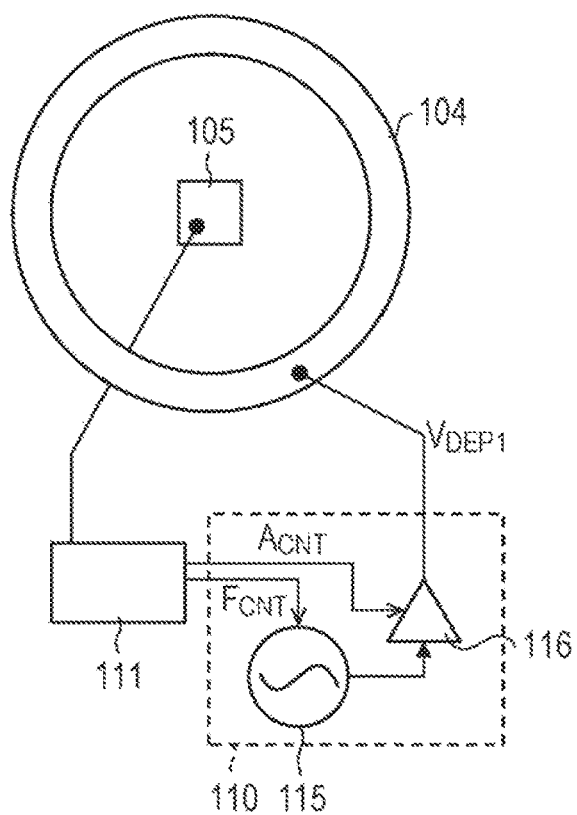
FIG. 4 is a schematic view illustrating an example of a configuration to capture the bioparticle.

The control circuit 110 outputs the signal amplitude or the signal frequency of the signal $V_{DEP1}$ so that the impedance difference detected by the sensor electrode 105 is fixed. For example, as illustrated in FIG. 4, the control circuit 110 performs control by outputting a signal $F_{CNT}$ with respect to a frequency of an oscillator 115 constituted by a ring oscillator or the like on the basis of a detection signal of the detection circuit 111. Regarding the frequency with which the bioparticle 106 is suspended in the solution 102, an upper limit and a lower limit of the frequency in the attraction direction and the repulsion direction are determined in advance and the frequency is adjusted by the signal $F_{CNT}$ in a range of the upper limit and the lower limit. An output amplitude of a buffer circuit 116 in the output of the oscillator 115 is controlled by outputting a signal $A_{CNT}$ from the detection circuit 111. The signal $V_{DEP1}$ is output from the control circuit 110 by using an external signal source (not illustrated).

According to the aforementioned configuration, with the signal amplitude or the signal frequency of the signal $V_{DEF1}$, the bioparticle 106 is suspended in the liquid without sinking due to gravity and by the negative dielectrophoresis force while keeping a certain fixed distance from the sensor electrode 105.

When determining the distance between the sensor electrode 105 and the bioparticle 106, the impedance difference between the solution 102 and the bioparticle 106 is measured by performing sensing using a dielectric constant difference between the solution 102 and the bioparticle 106. In this case, it is desirable to perform the sensing with a sensing frequency in the sensor electrode 105 higher than the frequency of the signal $V_{DEP1}$ used for dielectrophoresis. By measuring the dielectric constant difference between the solution 102 and the bioparticle 106 at the measurement frequency of the sensor electrode 105, the impedance is able to be measured without affecting the dielectrophoresis force $F_{DEP}$.

Though the dielectrophoresis electrode 104 may be formed to surround, in a circular shape, the sensor electrode 105 with the sensor electrode 105 located at the center as illustrated in FIG. 2A, a structure may be provided in which three dielectrophoresis electrodes 107 are arranged at intervals of 120 degrees with the sensor electrode 105 located at the center as illustrated in FIG. 2B. Further, a structure may be provided in which four dielectrophoresis electrodes 108 are arranged at intervals of 90 degrees with the sensor electrode 105 located at the center as illustrated in FIG. 2C. It is sufficient that the periphery of the sensor electrode 105 is surrounded with a dielectrophoresis electrode with the sensor electrode 105 located at the center.

[Capturing of Bioparticle]

Figure 3:
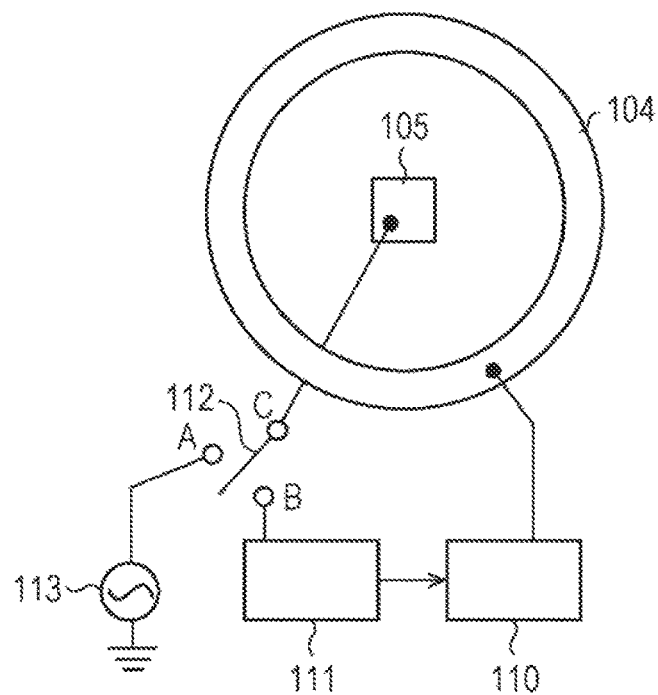
FIG. 3 is a schematic view illustrating an example of a configuration to capture a bioparticle in the bioparticle observation apparatus.

When the bioparticle 106 suspended in the solution 102 is captured in the center of the dielectrophoresis electrode 104, a positive dielectrophoresis signal $V_{DEP2}$ to capture the bioparticle 106 is applied to the sensor electrode 105. FIG. 3 illustrates an example of a configuration to capture the bioparticle 106. A terminal connected to the sensor electrode 105 includes a switch 112, and connection destinations of the switch 112 are a point A and a point B starting from a point C.

The point A is connected to a signal source 113. When the switch 112 is connected to the point A, the signal source 113 applies, through the switch 112 to the sensor electrode 105, the positive dielectrophoresis signal (second signal) $V_{DEP2}$ to capture the bioparticle 106. At this time, the detection circuit 111 and the control circuit 110 in which the switch 112 is switched off do not operate and in addition the dielectrophoresis electrode 104 does not operate, and as a result the bioparticle 106 is not affected by the dielectrophoresis electrode 104. When the switch 112 is connected to the point B, the signal obtained from the sensor electrode 105 is detected by the detection circuit 111 as illustrated in FIGS. 2A to 2C.

Figure 5:
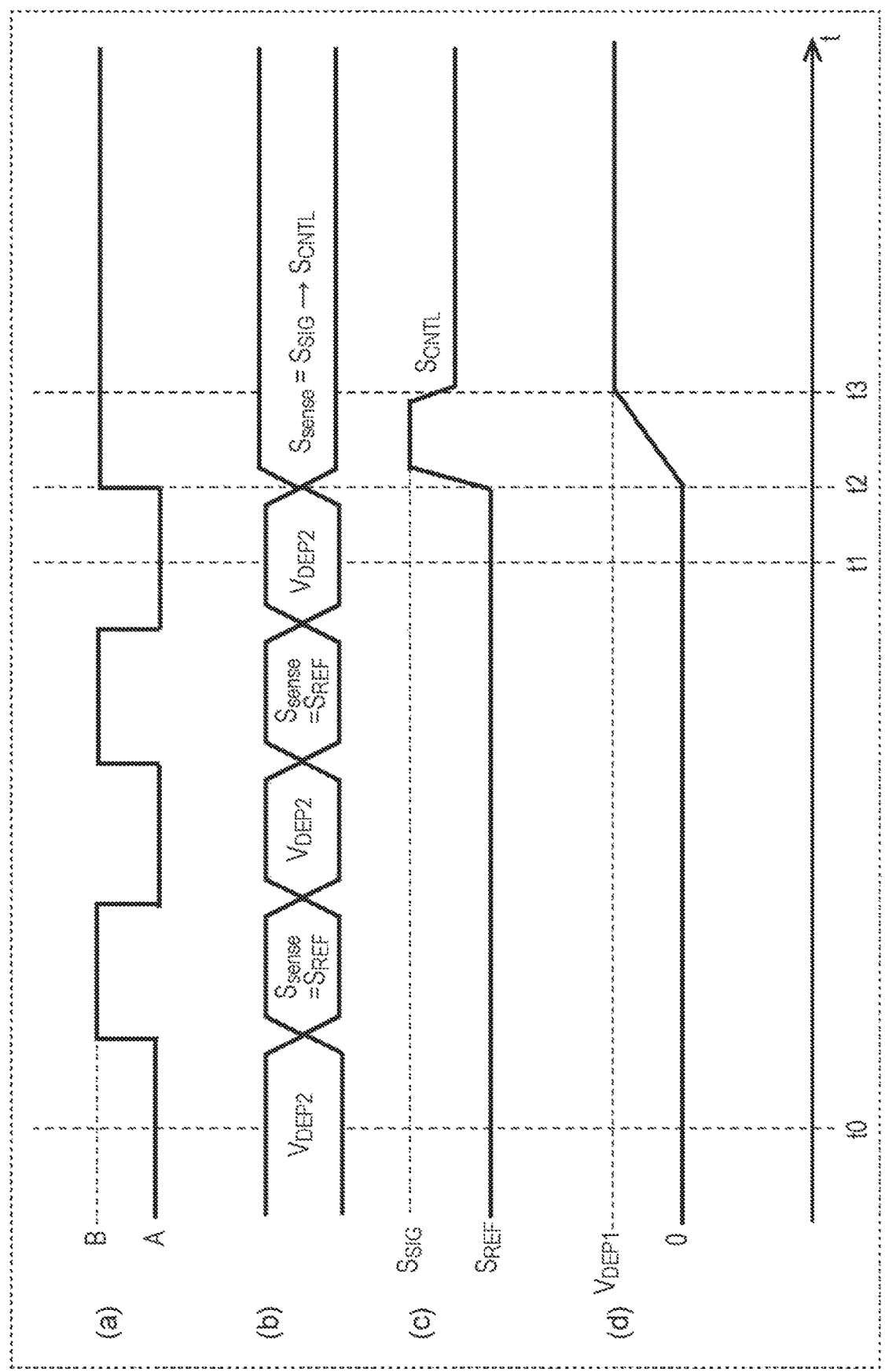
FIG. 5 is a timing chart when the bioparticle is captured by a sensor electrode in the bioparticle observation apparatus.

Next, a timing chart for capturing the bioparticle 106 in the sensor electrode 105 will be described with reference to FIG. 5. (a) of FIG. 5 illustrates an operation timing of the point C of the switch 112, and the switch 112 is alternately connected to the point A and the point B for a fixed period $t_0$ to $t_1$. As illustrated in (b) of FIG. 5, as a signal handled at the point C of the switch 112, the positive dielectrophoresis signal $V_{DEP2}$ is applied to the sensor electrode 105 or $S_{sense}$ is acquired by operating the detection circuit 111, and the application of the positive dielectrophoresis signal $V_{DEP2}$ and the acquisition of $S_{sense}$ are alternately performed through the operation of the switch 112 of (a) of FIG. 5.

The period $t_0$ to $t_1$ indicates an example of a state where the bioparticle 106 is not captured, and when the switch 112 is connected to the point B, the signal $S_{sense}$ detected by the sensor electrode 105 is $S_{sense}=S_{REF}$ as a signal calculated using the dielectric constant of the solution 102.

A value of the signal $S_{REF}$ calculated using the dielectric constant of the solution 102 is stored in a memory (not illustrated) or the like attached to the detection circuit 111. Since the switch 112 is connected to the point A or the point B for a fixed period as illustrated in (a) of FIG. 5, when the switch 112 is connected to the point A, the positive dielectrophoresis signal $V_{DEP2}$ is applied to the sensor electrode 105.

Here, it is assumed that the sensor electrode 105 attracts the bioparticle 106 at a certain timing ($t_1$). Subsequently, when the switch 112 is connected to the point B ($t_2$), the sensor electrode 105 detects a signal $S_{SIG}$ calculated using the dielectric constant of the bioparticle 106. When it is determined that there is a difference between the values of $S_{SIG}$ and $S_{REF}$ because $S_{SIG}$ and $S_{REF}$ have different values as illustrated in (c) of FIG. 5, the switch 112 remains connected to only the point B.

At the same time, as illustrated in (d) of FIG. 5, the signal $V_{DEP1}$ by which the negative dielectrophoresis force acts on the dielectrophoresis electrode 104 is provided. At this time, the dielectrophoresis force that enables attraction to the sensor electrode 105 does not act on the bioparticle 106 but the dielectrophoresis force that enables repulsion is applied to the bioparticle 106 by the dielectrophoresis electrode 104 which surrounds the periphery of the sensor electrode 105, and as a result the bioparticle 106 moves (floats) in a direction (upper direction) away from the sensor electrode 105.

Since the bioparticle 106 is generally denser than the solution 102, when the solution 102 does not flow or flows very slowly, the bioparticle 106 sinks (is attracted to the sensor electrode 105), but at the time $t_3$ and thereafter, by providing the signal $V_{DEP1}$ of the appropriate negative dielectrophoresis force that enables repulsion via the dielectrophoresis electrode 104, the bioparticle 106 remains suspended above the sensor electrode 105 in the solution 102.

The signal $V_{DEP1}$ is a signal by which a position of the bioparticle 106 is adjusted so that a value ($=S_{CNTL}$) between $S_{SIG}$ and $S_{REF}$ illustrated in (c) of FIG. 5 is obtained from the sensor electrode 105. For example, control is performed in such a manner that, when $S_{CNTL}$ has a value larger than an appropriate value, the bioparticle 106 approaches the sensor electrode 105, and as a result, for example, the amplitude of the signal $V_{DEP1}$ is increased, and when $S_{CNTL}$ has a value smaller than the appropriate value, the bioparticle 106 moves away from the sensor electrode 105, and as a result the amplitude of the signal $V_{DEP1}$ is reduced.

According to the aforementioned configuration, when the dielectrophoresis force acts on the bioparticle 106, a single bioparticle 106 is able to be fixed at a predetermined position in a suspended state. Thereby, the bioparticle 106 is not fixed by protein or the like, and there is no physical contact with a surface of the bioparticle 106, thus making it possible to reduce damage to the bioparticle 106 and facilitate observation of the single bioparticle 106.

Embodiment 2

Another embodiment of the disclosure will be described below. Note that, for convenience of description, members having the same functions as those of the members described in the aforementioned embodiment will be given the same reference signs and description thereof will not be repeated.

Figure 6:
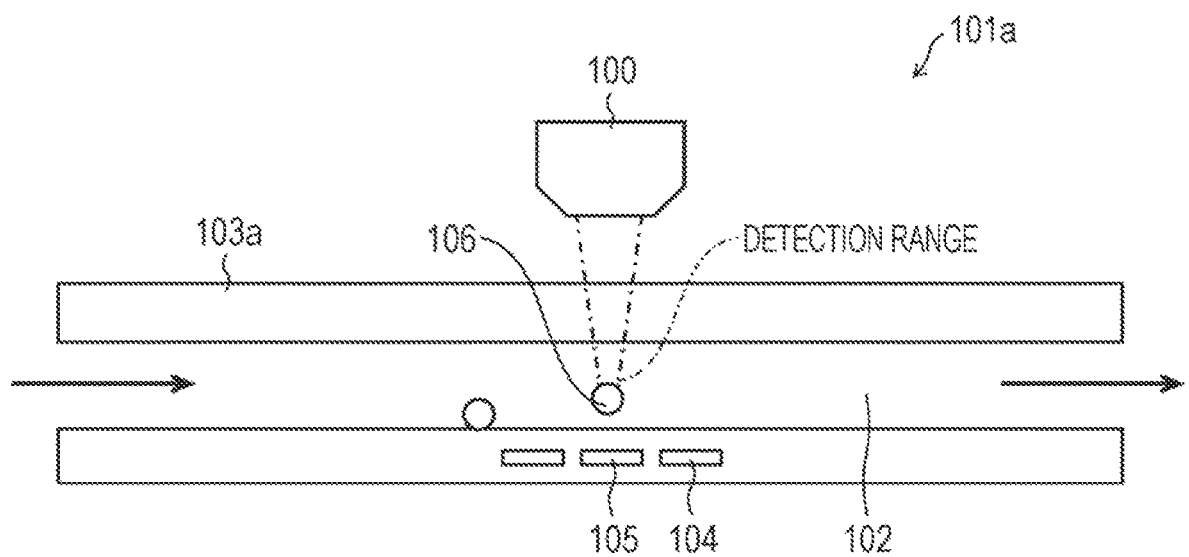
FIG. 6 is a schematic view illustrating an outline configuration of a bioparticle observation apparatus according to Embodiment 2 of the disclosure.
Figure 7:
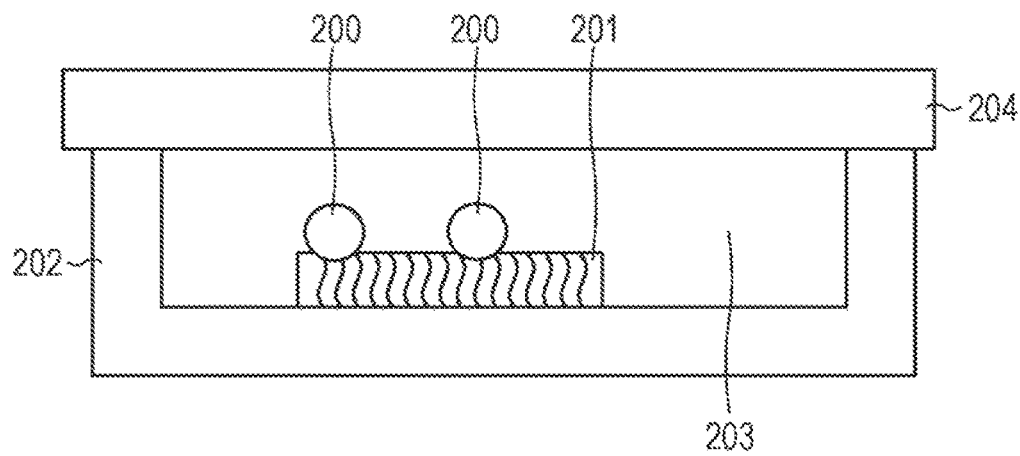
FIG. 7 is a schematic view for explaining a method of observing a bioparticle according to the related art.

In the aforementioned embodiment, an embodiment in which the container 103 is a container such as a Petri dish whose top surface is opened has been described. However, as in a bioparticle observation apparatus 101a of the present embodiment, a structure that causes the solution 102 to flow from upstream to downstream like a microfluidic channel 103a may be adopted (refer to FIG. 6) instead of the container 103. The bioparticle 106 flows in the microfluidic channel 103a.

In this case, it is desirable that a top surface of the sensor electrode 105 be made of a transparent material that enables check by the microscope 100. The flow of the solution 102 may be controlled so that a flow rate of the solution 102 changes, for example, by stopping the flow of the solution 102 or causing the solution 102 to flow slowly to such an extent that the bioparticle 106 does not move away from above the sensor electrode 105 in the center of the dielectrophoresis electrode 104, after the time $t_1$ when the bioparticle 106 is captured as described in FIG. 5.

CONCLUSION

A bioparticle observation apparatus according to an aspect 1 of the disclosure is a bioparticle observation apparatus usable for observation of a bioparticle in liquid, and includes: a dielectrophoresis electrode that outputs a first signal causing a dielectrophoresis force to act on the bioparticle; a sensor electrode that detects an impedance difference between the bioparticle and the liquid; and a control circuit that controls the first signal so that the detected impedance difference is fixed.

According to the aforementioned configuration, when the dielectrophoresis force is caused to act on the bioparticle, the single bioparticle is able to be fixed at a predetermined position in a suspended state. Thereby, the bioparticle is not fixed by protein or the like and there is no physical contact with a surface of the bioparticle, thus making it possible to reduce damage to the bioparticle and facilitate observation of the single bioparticle.

In the bioparticle observation apparatus according to an aspect 2 of the disclosure, it is desirable that the control circuit controls an amplitude or a frequency of the first signal in the aspect 1. According to the aforementioned configuration, when the control circuit controls the amplitude or the frequency of the first signal output from the dielectrophoresis electrode, the bioparticle floats in the liquid without sinking due to gravity and a negative dielectrophoresis force while keeping a certain fixed distance away from the sensor electrode.

In the bioparticle observation apparatus according to an aspect 3 of the disclosure, the dielectrophoresis electrode may have a circular shape or a polygonal shape to surround a periphery of the sensor electrode with the sensor electrode located at a center and output a signal, which provides a negative dielectrophoresis force, as the first signal to the bioparticle, in the aspect 1 or 2. According to the aforementioned configuration, since the dielectrophoresis force near the sensor electrode acts in a direction to enable attraction to the sensor electrode or in a direction to enable repulsion from the sensor electrode in accordance with a size of an electric field provided by the dielectrophoresis electrode, and therefore it is possible to cause the bioparticle to stay in a part surrounded by the dielectrophoresis electrode.

In the bioparticle observation apparatus according to an aspect 4 of the disclosure, the dielectrophoresis electrode may include a plurality of electrodes arranged to surround a periphery of the sensor electrode with the sensor electrode located at a center and may output a signal, which provides a negative dielectrophoresis force, as the first signal to the bioparticle, in the aspect 1 or 2. According to the aforementioned configuration, it is possible to cause the bioparticle to stay in a part surrounded by the dielectrophoresis electrode.

In the bioparticle observation apparatus according to an aspect 5 of the disclosure, the sensor electrode may be a single electrode or a differential electrode, in any one of the aspect 1 to the aspect 4.

In the bioparticle observation apparatus according to an aspect 6 of the disclosure, it is desirable that the sensor electrode is connected to a switch and is able to switch, through the switch, between a function of detecting the impedance difference and a function of outputting a signal, which provides a positive dielectrophoresis force, to the bioparticle, in any one of the aspect 1 to the aspect 5. According to the aforementioned configuration, it is possible to capture the bioparticle, which floats in the liquid, in the center of the dielectrophoresis electrode.

In the bioparticle observation apparatus according to an aspect 7 of the disclosure, it is desirable that a second signal that provides a positive dielectrophoresis force is output from the sensor electrode, in any one of the aspect 1 to the aspect 6. According to the aforementioned configuration, it is possible to capture the bioparticle.

It is desirable that the bioparticle observation apparatus according to an aspect 8 of the disclosure further includes a microscope that enables observation from outside of a state where the bioparticle stays at a predetermined position, in any one of the aspect 1 to the aspect 7. According to the aforementioned configuration, it is possible to reduce damage to the bioparticle and facilitate observation of the single bioparticle.

The bioparticle observation apparatus according to an aspect 9 of the disclosure may further include a microfluidic channel in which the bioparticle flows, in any one of the aspect 1 to the aspect 8.

A bioparticle observation method according to an aspect 10 of the disclosure includes causing a bioparticle to stay at a predetermined position in liquid by using the bioparticle observation apparatus according to any one of the aspect 1 to the aspect 9, and observing a state where the bioparticle stays at the predetermined position from outside by using a microscope. According to the aforementioned method, it is possible to reduce damage to the bioparticle and facilitate observation of the single bioparticle.

[Other Expression of Disclosure]

The disclosure may be expressed as below. That is, a bioparticle observation apparatus according to an aspect of the disclosure is a bioparticle observation apparatus that causes a single fine bioparticle to stay at a predetermined position in liquid, includes a dielectrophoresis electrode and a sensor electrode, and has a configuration in which an impedance difference between the bioparticle and the liquid existing around the bioparticle is detected and a signal output from the dielectrophoresis electrode is controlled by a control circuit so that the bioparticle stays at the predetermined position in the liquid.

Moreover, in the bioparticle observation apparatus according to an aspect of the disclosure, it is desirable that the control circuit controls an amplitude or a frequency of the signal output from the dielectrophoresis electrode.

Moreover, in the bioparticle observation apparatus according to an aspect of the disclosure, it is desirable that the dielectrophoresis electrode has a circular shape or a polygonal shape to surround the sensor electrode with the sensor electrode located at a center and outputs a signal, which provides a negative dielectrophoresis force, to the bioparticle.

Moreover, in the bioparticle observation apparatus according to an aspect of the disclosure, it is desirable that the dielectrophoresis electrode includes a plurality of electrodes arranged to surround the sensor electrode with the sensor electrode located at a center and outputs a signal, which provides a negative dielectrophoresis force, to the bioparticle.

Moreover, in the bioparticle observation apparatus according to an aspect of the disclosure, the sensor electrode may be a single electrode or a differential electrode.

Moreover, in the bioparticle observation apparatus according to an aspect of the disclosure, the sensor electrode may include a switch circuit to have a function of detecting the impedance difference between the bioparticle and the liquid existing around the bioparticle and a function of outputting a signal, which provides a positive dielectrophoresis force, to the bioparticle.

Moreover, in the bioparticle observation apparatus according to an aspect of the disclosure, after a reference signal is detected from an impedance value in a state where the bioparticle is not captured in the sensor electrode and stored in a memory circuit, the switch circuit may be switched, and the bioparticle may be captured by outputting a signal, which provides a positive dielectrophoresis force, from the sensor electrode, and while keeping the capturing of the bioparticle by outputting a signal, which provides a negative dielectrophoresis force, from the dielectrophoresis electrode, a capturing signal may be detected from the impedance value of the bioparticle captured in the sensor electrode, and on the basis of the reference signal stored in the memory circuit and a setting signal set from the capturing signal, the signal which provides the negative dielectrophoresis force may be output from the dielectrophoresis electrode by controlling an amplitude or a frequency thereof so that the bioparticle stays at a predetermined position in the liquid, and thereby the bioparticle may stay at the predetermined position.

Moreover, the bioparticle observation apparatus according to an aspect of the disclosure may further include a microscope that enables observation from outside of a state where the bioparticle stays at a predetermined position.

APPENDIX

The disclosure is not limited to the respective embodiments described above and may be modified in various manners within the scope of the claim, and an embodiment achieved by appropriately combining techniques disclosed in each of different embodiments is also encompassed in the technical scope of the disclosure. Further, by combining the techniques disclosed in each of the different embodiments, a new technical feature may be formed.

The present disclosure contains subject matter related to that disclosed in Japanese Priority Patent Application JP 2018-111342 filed in the Japan Patent Office on Jun. 11, 2018, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A bioparticle observation apparatus usable for observation of a bioparticle in liquid, the bioparticle observation apparatus comprising:
    a dielectrophoresis electrode that outputs a first signal causing a dielectrophoresis force to act on the bioparticle;
    a sensor electrode that detects an impedance difference between the bioparticle and the liquid; and
    a control circuit that controls the first signal so that the detected impedance difference is fixed,
    a second signal that provides a positive dielectrophoresis force being output from the sensor electrode.

2. The bioparticle observation apparatus according to claim 1, wherein
    the control circuit controls an amplitude or a frequency of the first signal.

3. The bioparticle observation apparatus according to claim 1, wherein
    the dielectrophoresis electrode has a circular shape or a polygonal shape to surround a periphery of the sensor electrode with the sensor electrode located at a center and outputs a signal, which provides a negative dielectrophoresis force, as the first signal to the bioparticle.

4. The bioparticle observation apparatus according to claim 1, wherein
    the dielectrophoresis electrode includes a plurality of electrodes arranged to surround a periphery of the sensor electrode with the sensor electrode located at a center and outputs a signal, which provides a negative dielectrophoresis force, as the first signal to the bioparticle.

5. The bioparticle observation apparatus according to claim 1, wherein
    the sensor electrode is a single electrode or a differential electrode.

6. A bioparticle observation apparatus for observation of a bioparticle in liquid, the bioparticle observation apparatus comprising:
    a dielectrophoresis electrode that outputs a first signal causing a dielectrophoresis force to act on the bioparticle;
    a sensor electrode that detects an impedance difference between the bioparticle and the liquid; and
    a control circuit that controls the first signal so that the detected impedance difference is fixed,
    the sensor electrode being connected to a switch and being able to switch, through the switch, between a function of detecting the impedance difference and a function of outputting a signal, which provides a positive dielectrophoresis force, to the bioparticle.

7. The bioparticle observation apparatus according to claim 1, further comprising
    a microscope that enables observation from outside of a state where the bioparticle stays at a predetermined position.

8. The bioparticle observation apparatus according to claim 1, further comprising
    a microfluidic channel in which the bioparticle flows.

9. A bioparticle observation method, comprising:
    causing a bioparticle to stay at a predetermined position in liquid by using the bioparticle observation apparatus according to claim 1, and
    observing a state where the bioparticle stays at the predetermined position from outside by using a microscope.

10. The bioparticle observation apparatus according to claim 6, wherein
    the control circuit controls an amplitude or a frequency of the first signal.

11. The bioparticle observation apparatus according to claim 6, wherein
    the dielectrophoresis electrode has a circular shape or a polygonal shape to surround a periphery of the sensor electrode with the sensor electrode located at a center and outputs a signal, which provides a negative dielectrophoresis force, as the first signal to the bioparticle.

12. The bioparticle observation apparatus according to claim 6, wherein
    the dielectrophoresis electrode includes a plurality of electrodes arranged to surround a periphery of the sensor electrode with the sensor electrode located at a center and outputs a signal, which provides a negative dielectrophoresis force, as the first signal to the bioparticle.

13. The bioparticle observation apparatus according to claim 6, wherein
    the sensor electrode is a single electrode or a differential electrode.

14. The bioparticle observation apparatus according to claim 6, further comprising
    a microscope that enables observation from outside of a state where the bioparticle stays at a predetermined position.

15. The bioparticle observation apparatus according to claim 6, further comprising
    a microfluidic channel in which the bioparticle flows.

16. A bioparticle observation method, comprising:
    causing a bioparticle to stay at a predetermined position in liquid by using the bioparticle observation apparatus according to claim 6, and
    observing a state where the bioparticle stays at the predetermined position from outside by using a microscope.

* * * * *